United States Patent [19]
Tobin et al.

[11] Patent Number: 6,077,534
[45] Date of Patent: Jun. 20, 2000

[54] PRODUCTION OF PHARMACEUTICAL FORMULATIONS FOR TREATMENT OF EDEMA AND VENOUS DISORDERS

[75] Inventors: James Tobin, Killorglin Co. Kerry, Ireland; Gerd Ulfert Heese, Munich, Germany

[73] Assignee: Klinge Pharma GmbH, Munich, Germany

[21] Appl. No.: 08/921,694

[22] Filed: Sep. 2, 1997

[51] Int. Cl.$^7$ ........................................... A61K 9/62
[52] U.S. Cl. .................. 424/462; 424/488; 426/288
[58] Field of Search .................. 426/288; 424/462, 424/488

[56] References Cited

U.S. PATENT DOCUMENTS

| | | | |
|---|---|---|---|
| 2,702,264 | 2/1955 | Klaui | 424/482 |
| 3,139,383 | 6/1964 | Neville | 424/462 |
| 3,450,691 | 6/1969 | Wagner et al. | 260/210.5 |
| 4,707,360 | 11/1987 | Brasey | 494/94.1 |
| 5,080,901 | 1/1992 | Hangay et al. | 424/195.1 |
| 5,578,307 | 11/1996 | Wunderlich et al. | 424/195.1 |

FOREIGN PATENT DOCUMENTS

| | | |
|---|---|---|
| 3643000 | 6/1988 | Germany . |
| 196 29 040 A1 | 1/1998 | Germany . |

OTHER PUBLICATIONS

HCAPLUS 1983: 443529 Bonati #77 3517 Switz. Mar. 1983.

Ditten M. et al, Úntersuchung der Bioverfugbarkei von beta–Aescin nach oraler Verabreichung verschiedener Darreichungsformen vol. 51, No. 8, 1996, pp. 608–510, XP002084541.

"Rote Liste", 1997 Editio Cantor, Aulendorff/Wurtt, XP002084542, Nr. 83032, 83033.

Rote Liste (German Physician's Desk Reference) 1967: "Wenostasin".

Rote Liste 1974: "Venostasin Regard", No. 91001.

Monographie DAB 10, vol. 2 (1993): "Hippocastani extractum siccum normaturn".

Isaac Ghebre–Sellassie: "Pharmaceutical Pelletization Technolgy", NY (1989).

Med. Welt, Bd. 32, Nr. 51/52 (1981), S. 1953–1955.

*Primary Examiner*—Neil S. Levy
*Attorney, Agent, or Firm*—Sughrue, Mion, Zinn, Macpeak & Seas, PLLC

[57] ABSTRACT

The invention relates to a medicament containing a standardized dry extract of horse chestnut seeds which is active against various types of edema and diseases of the venous circulatory system and to a process for manufacturing this medicament. The dry seed extract is processed to the form of pellets which can be coated to obtain sustained release of the agent. In this way satisfying therapeutical blood levels of the triterpene glycosides as agent are achieved. The finished medicament according to the invention can best be provided as hard gelatin capsule or matrix tablet containing the extract pellets.

11 Claims, 4 Drawing Sheets

PRODUCTION OF PHARMACEUTICAL FORMULATIONS FOR TREATMENT OF EDEMA AND VENOUS DISORDERS

BACKGROUND TO THE INVENTION

Medicaments containing horse chestnut extract (HCE) are usually derived from horse chestnut seeds, i.e. semen of *Aesculus hippocastanus*. Such medicaments have been described in pharmaceutical literature, for instance in the German physician's desk reference "Rote Liste" (1967), page 1333. Pharmaceutical products containing horse chestnut extract (HCE) have been manufactured and administered in the form of soft gelatin capsules, ointments, liquid formulations, ampuls or vials for injection, dragées or suppositories.

Many scientific investigations have been carried out in order to establish the active ingrdient in the horse chestnut extract (HCE), that is, the agent responsible for the biological effect on the venous system. These investigations have revealed that escin, a specific triterpene glycoside, is the essential agent of pharmacological action. In animal model and human pharmacological model it has been demonstrated that, after administration of the horse chestnut extract (HCE), the permeability of the capillary vessel involved in venous and edemic disorders is decreased by 22% compared with the untreated or placebo-treated control, see Paschinger, E. Wirz and E. Zwerger, Med. Welt, 32, (1981), pgs. 1954 et sequ. Studies carried out on horse chestnut administration to treat post-traumatic edema such as edemae after injuries, brain edema, thrombophlebitis or other disorders of the venous circulatory system (for instance venous insufficiency) it revealed that the quality and action of those conventional simple compositions were not satisfactory. It was recognized that the release rate of the active ingredient needed improvement because of its irregular and unreliable behaviour in the blood stream and its short lasting action. Prolonged action and regular therapeutical levels in the blood stream (when the medicament is administered in solid form) can be achieved in a number of different ways. For example, multi-layer tablets, embedded or matrix forms, molded tablets, extrusion, "mantled" tablets or so-called pellet preparations all of which after administration show more or less sustained agent release in different sections of the gastro-intestinal tract according to the specific drug designs and characteristics of the agent and ingredients as well as the particular preparation technique.

Since the early 1950s attempts were made to develop extended release products. Since then, the manufacture of pellets has been the subject of intensive research, in particular with the development of innovative formulations. Conventionally, the word "pellet" has been used to describe a variety of systematically produced geometrically defined agglomerates comprising the drug and different ingredients such as binding agents, carriers and, if necessary, specific coatings. Pelletization inter alia is an agglomeration process that converts fine powders or granules of bulk drugs and excipients into small, free-flowing, spherical or semi-spherical units which are referred to as pellets. They range in size, typically, between 500 to 1500 $\mu$m, but diameters of less than 500 $\mu$m can also be used. Some of the most widely used pelletization processes in the art are extrusion or spheronization methods. In addition to this process solution/suspension layering or powdered layering are also utilized.

Pellets have great importance in pharmaceutical industry for various reasons. Pelletized products not only show flexibility in dosage form, design and development, but are also utilized to improve the safety and potential of an almost ideal bioavailability of drugs. When pellets containing the active ingredient are administered in vivo in the form of suspension, capsules or disintegrating tablets, they have significant therapeutic advantages over single-unit dosage forms.

Because pellets disperse freely in the gastrointestinal tract, they maximize drug absorption, reduce peak plasma fluctuations and minimize potential side effects without notably lowering drug bioavailability.

This kind of unit dosage form also reduces variations in gastric emptying rates and overall transit times. In this way the undesirable variability of plasma profiles which are common with other conventional dosage forms such as single-unit medicaments in the form of simply compacted tablets or dragée cores, are minimized. A further advantage of pellets over the conventional single-unit dosage forms as indicated above is that high local concentrations of drugs which may inherently be irritative or anaestethic with conventional sustained release medicaments can be avoided.

Controlled release pellets are prepared either to deliver the drug at a specific site within the gastrointestinal tract or to sustain the action of drugs over an extended period of time. Another advantage of manufacturing pellets is an enormous flexibility during the development of oral dosage forms, for instance, pellets composed of different drug entities can be blended and formulated in a single dosage form. This procedure allows the combined delivery of two or more drugs that may or may not be chemically compatible, to the same or different sites within the gastro-intestinal tract. A combination of pellets of different drugs, optionally having different release rates, administered as a single dose may be delivered to the same area or optionally to different sections of the gastrointestinal tract. Furthermore, pellets have a low surface area-to-volume ratio and provide an ideal shape for the application of film coatings. It is important that pellets of reproducible weights for charging capsules can be achieved in order to conform to the FDA's Good Manufacturing Practice (GMP) Regulations.

As alternatives to the above pelletization processes are other conventional methods including conventional such as globulation, balling or compression.

As a first pelletization step, a conventional granulation process is followed by globulation or spheronization is used. However, various problems arise depending on the specific drugs to be pelletized. In particular plant extracts tend to agglomerate before processing usually because of their hygroscopicity. Further problems may arise in coating the pellets to achieve sustained release and to obtain reproducible release rates. Matrix pellets may be used instead of coated pellets. Matrix pellets have the drug embedded in a matrix of lipid substance or polymers where one or more bioactive agents is set free within the gastrointestinal tract by erosion. In contrast to this erosion form, the active ingredient is released across the fine pored water-insoluble, permeable coating membrane of the above said coated pellet, the coating, for instance, consisting of polymers built up by unsaturated organic acid monomer units.

This form shows a mechanism which is substantially uneffected by pH, ion concentration or enzyme activity in the gastro-intestinal tract. Coated pellets having this pH-independent release mechanism are called diffusion pellets which following their uptake are distributed within the gastro-intestinal tract and gradually release the respective agent through the micropores of a suitable polymeric coating.

Among the above pharmaceutical compositions containing horse chestnut extract (HCE) the pellet form was chosen to study its applicability for developing a medicament on the basis of that plant extract having an improved quality, in particular superior drug safety and bioavailability. It has been demonstrated that the choice for an pH-independent agent release system, that is a coated pellet form, causes a series of further problems and drawbacks. Investigations carried out have shown that the type and composition of the horse chestnut extract (HCE) and additives used to form and spheronize the pellets, presents problems to the pellet surface consistency, that is its uniformity, for instance concerning its ideal ball or globule shape.

The pellet processing usually leads to irregular, uneven and coarse surfaces and a broad mean grain distribution of the pellets to be manufactured. It also leads to mechanical problems such as blocking of machine parts or undesired agglomerations during pelletizing. Conventional horse chestnut extracts (HCE) obtained by drying the extracted seed material over heated drums or under reduced pressure in heated boxes are especially prone to cause considerable mechanical pelletizing problems which can result in blocked apparatus. This results in lost batches and unproductive working hours. Those conventional pelletizing processes employing common extract materials have been found to be very expensive and uneconomical. Furthermore, the drug safety was not found to be satisfactory and the desired release rates were not obtained.

Studies have revealed that there are many problems associated with irregular pellet form and surface which lead to unforseeable disadvantageous properties of the finished pellets. It has been found that the problems also influence the release rates so that a substantial quantity of successfully pelletized material made of conventionally dried seed extract is rejected because of batches that do not conform to the necessary drug quality standards. This is the case for the coated sustained release pellets made of conventionally prepared seed extract having an irregular shape. These drawbacks lead, inter alia, to problems in encapsulating the pellets containing the active ingredient or principle by causing undesired dosage deviations. Furthermore it has been recognized that these problems impair the drug quality and safety in addition to economical losses, undue energy consumption, machine down-time (in which machines are out of action for long periods after blockage and during cleaning) and additional wage costs etc.

OBJECTS OF THE INVENTION

Therefore a first object of the present invention is to provide a method permitting the standardization of horse chestnut extract (HCE) pellets.

A further object of the present invention is to provide a method of producing superior quality pellets containing escin as active ingredient, which pellets have improved safety and optimized bioavailability (permitting the provision of continuous therapeutical blood levels in a reproducible manner).

It is still further object of the invention to provide a pharmaceutical formulation containing horse chestnut extract (HCE) which has enhanced quality, consistency and surface properties.

Yet a further object of the present invention is to permit the manufacture of a pharmaceutical composition containing escin in economical manner in such a way that the formulation can approximate to the desired ideal effect in the therapeutical treatment of post-traumatic edema and disorders of the venous circulatory system.

A further object of the invention is to provide a horse chestnut extract (HCE) formulation whose active unit dosages can have minimum weight and dimensions so that the patients compliance is not disturbed by large tablets or capsules to ingest. On the other hand, minimum weight and dimensions of the pharmaceutical packages would save weights to be transported and stored so that energy consumption could be reduced for ecological and economical reasons. In this context the ecological aim to reduce the overall quantity of waste, which worldwide is an increasingly serious problem.

SUMMARY OF THE INVENTION

The objects of the invention can be achieved according to the invention by a method of producing a pharmaceutical formulation (suitable for administration, inter alia, in capsule form), the formulation containing escin as the pharmaceutically active ingredient, for treatment or prophylaxis of venous circulatory disorders, various types of edema, or inflammation. The formulation is prepared by a process comprising the following steps:

(a) solvent extracting of horse chestnut seeds;
(b) mixing the resultant solvent extract with dextrin;
(c) drying the resultant mixture to particulate form;
(d) blending the particulate mixture with further dextrin, a pharmaceutically acceptable binder and a pharmaceutically acceptable filler,
(e) pelletizing the resulting blend as pellets having a particle size in the range 500–1700 micrometers; and
(f) coating the resulting pellets, in substantially dry form, with a pharmaceutically acceptable acrylate polymer.

The above method provides pellets with sustained release of the active ingredient in the blood stream by providing coated pellets. They are suitable for the production of formulations for the therapeutical and prophylactical administration in case of the above medical indications, in particular also to patients suffering from brain edema or swellings of different genesis.

DESCRIPTION OF PREFERRED EMBODIMENTS 1) preparing the dried horse chestnut extract (HCE) via steps (a) to (c):

i) milling the horse chestnut seeds to a maximum particle size of 6 mm and a minimum particle size of 0.3 mm, then macerating and percolating the milled seeds by a mixture of alcohol and water as solvent the alcohol content being 35–65% v/v during 1 to 2 days the temperature being 30–40° C. (86 to 104° F.) to obtain a horse chestnut extract (HCE) tincture, whereby 1500 kg–2000 kg seed material is extracted by 4000 to 5000 liters total solvent;

ii) concentrating the thus obtained liquid horse chestnut tincture under reduced atmospheric pressure by evaporation with a temperature of 45–60° C. (113 to 140° F.) until a content of total dry residue of 50% to 63% w/w in the liquid extract is obtained;

iii) adding dextrin in a ratio of 1 to 20 kg per 100 kg total dry substance calculated on the basis of the liquid extract obtained according to preceding step ii), optionally together with demineralized water in such an amount as to adjust the spray-drying solution to a total dry substance content of 38–48% w/w and a triterpene glycoside content of 15–20% w/w % in the dry extract to be made, calculated on the basis of the typical pharmacologically active agent escin, to prepare the liquid extract for spray-drying iv) spray-drying of the preceding liquid mixture at a temperature of 40–60° C. (104 to 140° F.), the inlet air having a O₂ content of <10% and a temperature of 180–210° C. (356 to 410° F.), the outlet air having a temperature of 75–95° C. (167 to 203° F.);

2) reparing the pellets via steps (d) and (e):

v) adding
   a) 10–30 parts by weight dextrin to
   b) the free-flowing spray-dried extract obtained through preceding step iv) up to an amount of 90–70 parts by weight total dry substance so that the complete mixture to be pelletized has a total standardized content of 15–19% w/w triterpene glycosides, calculated again on the basis of the typical agent escin;

vi) blending the above standardized mixture of a) dextrin and b) spray-dried extract together with
   c) polyvinylpyrrolidone, i.e. povidone or a copolymer of vinyl pyrrolidone and vinyl acetate having a mean molecular weight of 40 000 to 80 000 (calculated by the light dispersion method and
   d) talcum so that the weight ratio is in w/w 0.5–10 parts a): 50–150 parts b): 1–15 parts c): 0.5–10 parts d);

vii) granulating/pelletizing the mixture of a): b): c): d) by adding an alcohol for moistening the blend in a mixer/granulator apparatus or marumerizer, spheronizer or other commercial pelletizing machine;

viii) drying the moist pelletized material in a drier using a diverted recirculating air stream from the drier wherein the inlet temperature should not succeed 70° C. (158° F.) the outlet end point temperature being at least 45° C. (113° F.);

ix) sieving the dried pellet material to obtain a specification range of 500–1700 μm;

3) coating the pellets via step (f) to obtain their prolonged action:

x) coating the sieved pellets by spraying technique by means of a mixture of acrylates, for instance poly (ethylacrylate, methacrylate trimethyl-ammonioethylmethacrylate chloride having a mean molecular weight within the range of 120 000 to 180 000, dissolved in a mixture of organic solvents together with small amounts of a plastisizer such as triacetin, triethyl citrate or dibutyl phthalate so that the portion of the coating calculated on the basis of the total pellet weight is within the range of 2.5. to 5.0% w/w and finally 4) preparing the final medicament:

xi) filling the coated pellets into hard gelatin capsule bottom parts, closing the capsules by means of the gelatin top parts and then sealing into blister packages or alternatively producing a sustained release matrix tablet by compacting the said coated pellets together with pharmaceutically acceptable usual ingredients such as a desintegrating matrix carrier. Those formulations may optionally contain together further different agents in the form of pellets or processed in their respective powdery form.

The amount of pellets to be encapsulated or compacted to tablets is calculated in such a way that each capsule contains 20, 25, 30, 50, 75, 100 or 150 mg triterpene glycosides as agent which is calculated as escin, i.e. 200 mg pellet material can be filled into relatively small capsules if the triterpene glycoside content is only 15%, see step v)-b) to achieve a dosage amount of 30 mg agent or, for instance, approximately 278 mg coated pellets to encapsulate are sufficient to give a sustained release dosage unit of 50 mg triterperpene glycoside calculated as escin if the triterpene content of the coated pellet is in the upper limit of 18%.

The combination of steps and materials used to produce the pellets, together with the specific formula for the calculation of the amount of material needed at the various stages, all aid the production of pellets with improved release rates, surface properties, high yields and a better quality drug performance. The standardization of the triterpene glycosides contained within the extract help produce batch to batch consistency which is a guaranty for the uniformity of dosages. It is specifically the addition of dextrin to at least one stage, preferably in defined and calculated proportions and amounts, that enhances the drug safety and improves the properties of the pellets.

According to the invention, dextrin is used to prepare the dry extract from horse chestnut seeds to obtain a free-flowing which is standardized in terms of the active ingredient escin (which is used as a reference substance). Dextrin also renders the dry extract blend suitable for the subsequent pelletization step. Dextrin can be used for a two-step standardization on the basis of escin. Optionally the major amount of dextrin, which is used as standardizing amount and additive in both steps, may be added to the pelletization blend.

The particular steps, proportion and amounts of dextrin as processed according to the invention also improves the flowing and pelletizing properties of the horse chestnut extract (HCE) considerably. Inspite of improved properties, no problems of demixing of the pellets have been found. Surprisingly dextrin has a positive impact at high densities and compacting of the extract so that globulizing to form pellets with a high density with improved resistance to abrasion or trituration is notably improved.

By the method according to the invention an ideal pharmaceutical composition for the treatment of various forms of edema, disorders and diseases of the venous circulatory system, swellings or tumefactions, inflammations or for the enhancement of the anticoagulant action is provided.

Figure 1:
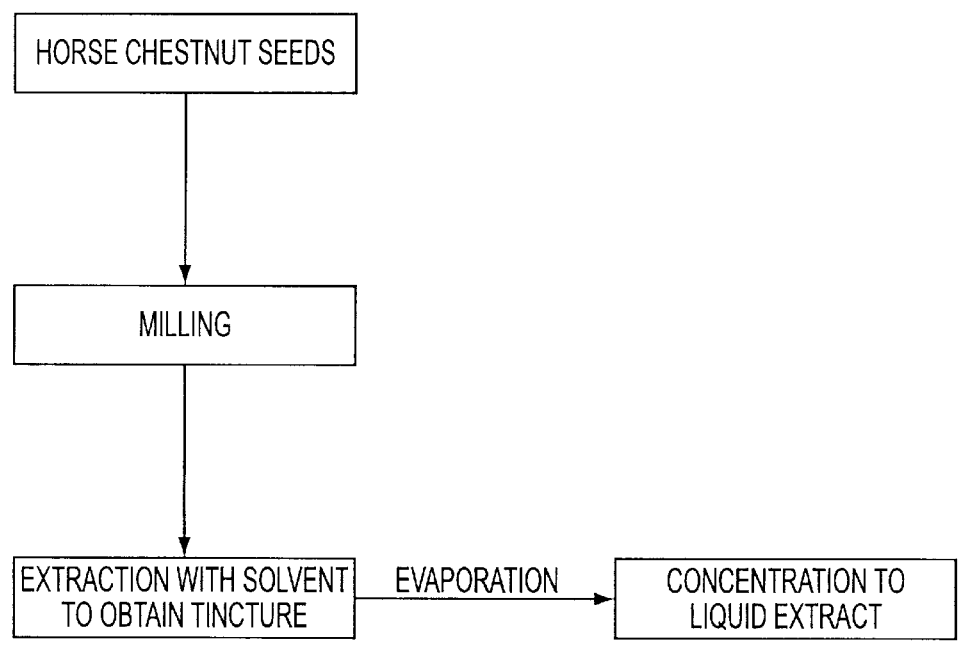
FIG. 1 shows a flow diagram displaying the preparation of the liquid extract of horse chestnut seeds by means of a watery solvent mixture and evaporation of the tincture obtainable by macerating and percolating the milled horse chestnut seeds in accordance with the invention as reflected by above described steps i) to ii)
Figure 2:
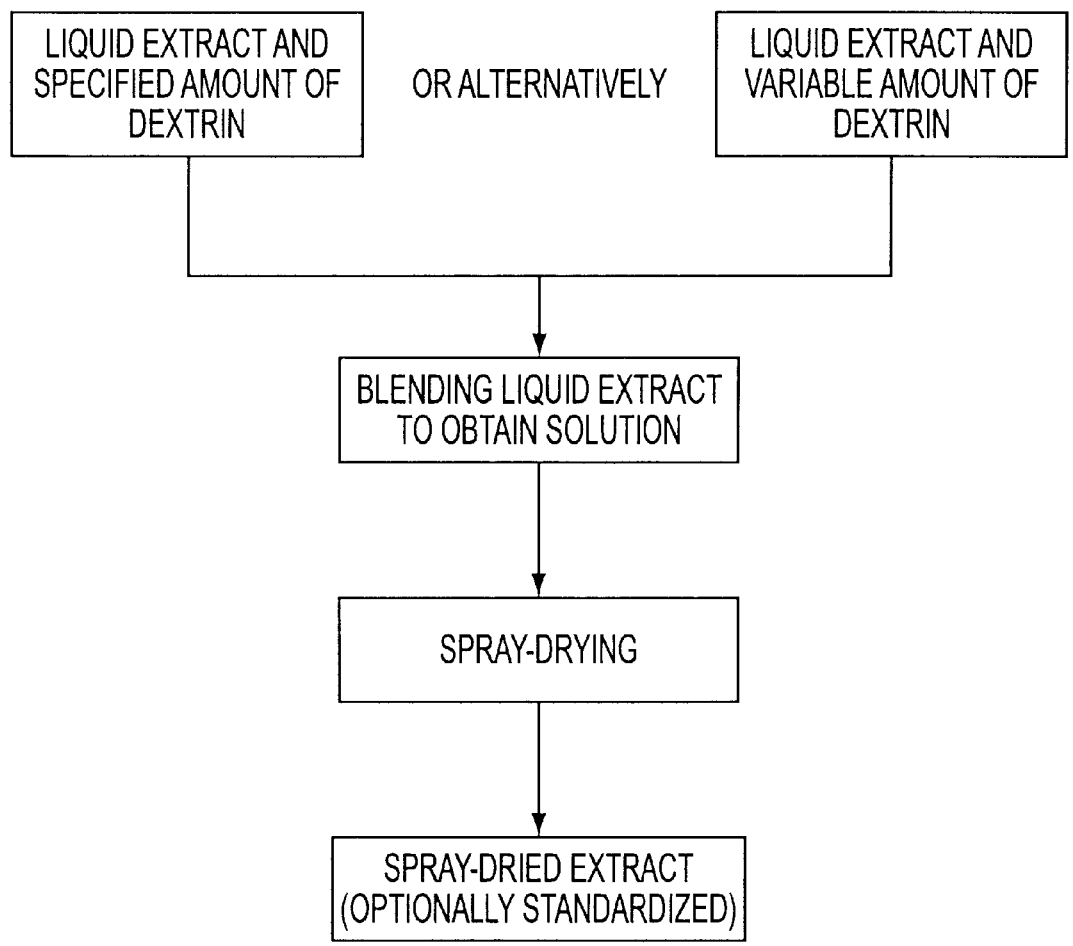
FIG. 2 shows in accordance with the invention the preparation of the free-flowing spay-dried extract of horse chestnut seeds including alternate features of adding major or minor amounts of dextrin, the latter being optionally a standardization additive as reflected by above steps ii) to iv)
Figure 3:
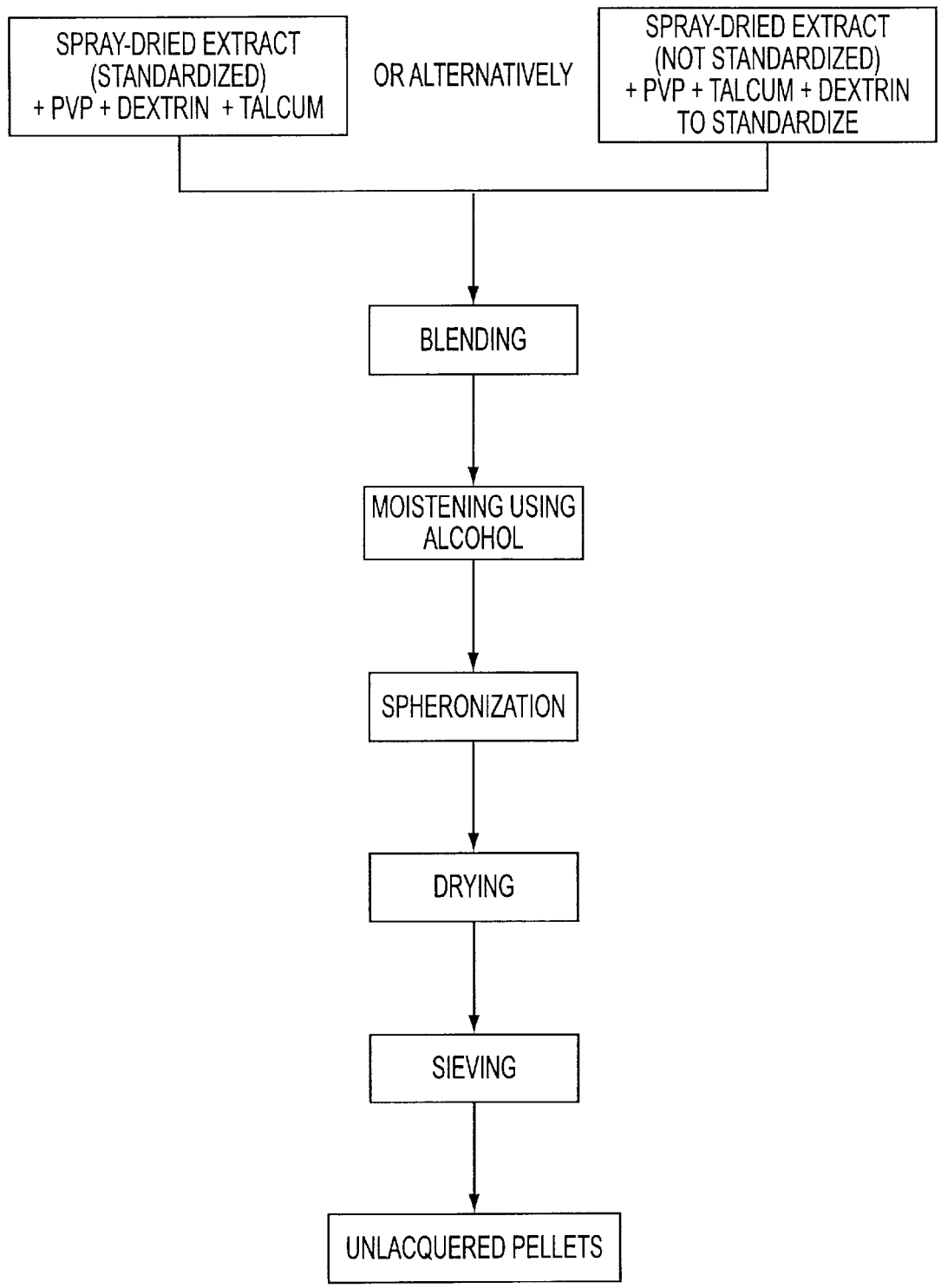
FIG. 3 shows the preparation of the uncoated, i.e. unlacquered horse chestnut extract pellets containing triterpene glycosides as agent, the standardization thereof being based on alterative routes according to steps v) to ix) in accordance with the invention.
Figure 4:
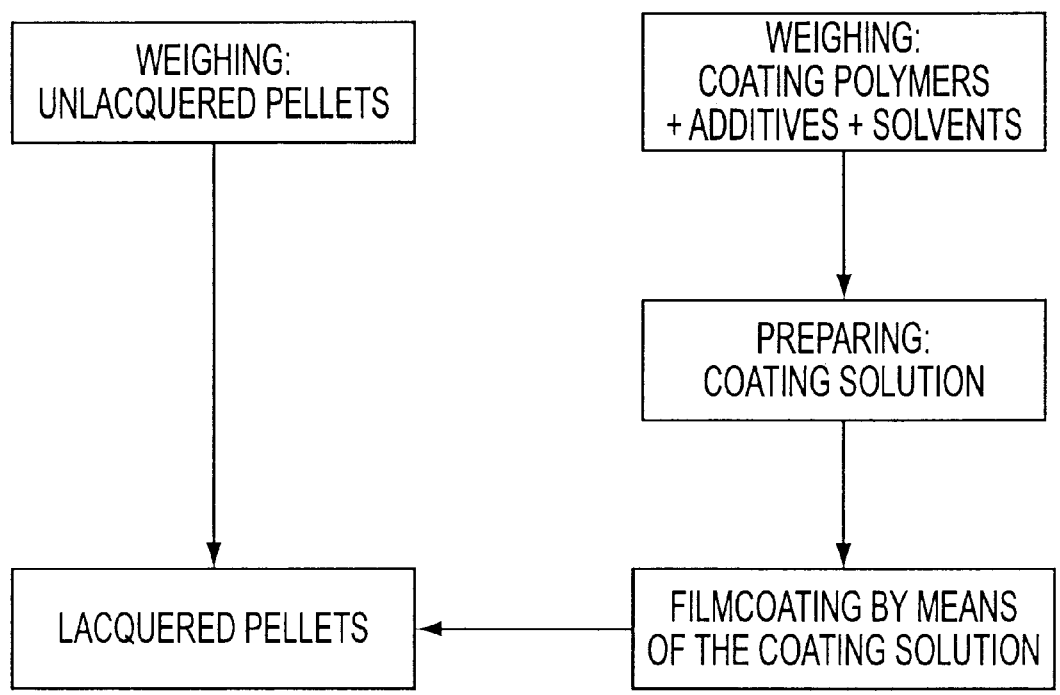
FIG. 4 shows the coating, i.e. lacquering the horse chestnut seed extract pellets to give sustained release form which may be used for the manufacture of the medicament ready for administration.

More specifically, the method according to the invention consists in the following manufacturing steps which are illustrated below in more detail:

DETAILED DESCRIPTION OF THE INVENTION

1) Preparation of the dried horse chestnut extract (HCE):
   i) the horse chestnut seeds are milled to give a size of between 6 mm and a minimum particle size of 0.3 mm, but preferably to a size range of 5.0 to 1.0 mm. This is carried out in a conventional plant drug cutting mill. The milled horse chestnut seeds are then over a period of 1 to 3 days, preferably 2 days macerated and percolated using a mixture of alcohol and demineralized water as the solvent with the alcohol content being 35–65% v/v, but preferably 40 to 45% v/v isopropanol, ethanol or methanol and the temperature being 30–40° C. (86 to 104° F.). The result is a horse chestnut extract (HCE) tincture, whereby 1500–2000 parts by weight, for instance 75–100 kgs seed material, preferably 1750 parts by weight seeds are extracted with 4000 to 5000 parts by volume, for instance 200 to 250 liters, preferably 4500 parts by volume total solvent (whereby on the basis of the cgs-system instead of kilograms and liters also for instance grams and milliliters may be meant). The end-tincture is left standing overnight so that insoluble particles may be decanted and the resulting the cleared tincture is filtered using a conventional chamber press.
   ii) The liquid horse chestnut tincture obtained is concentrated under reduced atmospheric pressure by evaporation in a conventional film evaporator at a temperature of 46–60° C. (113 to 140° F.), preferably at 55° C. (131° F.), until a content of total dry residue of 50% to 63% w/w, for instance 57% w/w, in the liquid extract is obtained.
   iii) The dextrin is then added to the liquid extract being concentrated in a ratio of 2 to 25 parts by weight, preferably 4 to 12 parts by weight per 100 parts by weight total dry substance calculated on the basis of the preceding liquid extract, optionally—depending on a high percentage of dry substance in the above liquid concentrated extract—demineralized water is added to the mixture of liquid extract plus dextrin in such an amount as to adjust the spray-drying solution to a total dry substance content of 38–48% w/w, preferably 42–46% w/w and a triterpene glycoside content of 15–20% w/w, preferably 17–19% w/w in the dry extract comprising the total dry substance to be made, calculated on the basis of the typical pharmacologically active agent escin, to prepare the liquid extract for spray-drying;
   whereby a major amount of dextrin, for instance 25 parts by weight, is used if the content of triterpene glycosides is standardized before spray-drying and vice versa, a minor amount of dextrin is incorporated in the spraying solution if the standardization of the triterpene glycosides calculated as escin is carried out in the next feature 2) to manufacture the extract pellets;
   iv) the preceding liquid mixture is spray-dried at a solution temperature of 40–60° C. (104 to 140° F.), preferably 45–55° C. (113 to 131° F.), the inlet air having a $O_2$ content of <10% and a temperature of 180–210° C. (356 to 410° F.), preferably 190–205° C. (374 to 401° F.), the outlet air having a temperature of 75–95° C. (167 to 203° F.), preferably 80–92° C. (176 to 198° F.);

2) preparation of the horse chestnut pellets:
   v) the material to be pelletized is mixed as follows:
      a) 0.5–20 parts per weight, preferably 1–10 parts per weight dextrin together with
      b) the free-flowing spray-dried extract obtained through preceding step iv) up to an amount of 90–70 parts per weight total dry substance so that the complete mixture to be pelletized has a total standardized content of 15–19% w/w, preferably 16–18% w/w triterpene glycosides, calculated again on the basis of the typical active agent escin;
   vi) the above standardized mixture of a) dextrin and b) spray-dried extract is further blended thoroughly together with
      c) polyvinylpyrrolidon, i.e. povidone or preferably a co-polymerisate of vinyl pyrrolidone and vinyle acetate, i.e. polyvidone acetat or co-povidone having a mean molecular weight of 40 000 to 80000, preferably 45 000 to 75 000 of VP/VA-copolyrmerisate 60/40 (calculated by the light dispersion method) and
      d) talcum so that the weight ratio is in w/w preferably 1–6 parts dextrin a): 60–100 parts free-flowing spray-dried extract b): 2–10 parts PVP or co-polymerisate c): 1–5 parts talcum d);
   vii) subsequently the powdery mixture of a): b): c): d) as manufactured according to preceding step vi) is moistened with
      e) alcohol, preferably isopropanol, in a mixer/granulator apparatus or marumerizer, spheronizer or other conventional pelletizing machine, preferably a commercial high shear mixer up to an amount of approximately 15–30 parts d) w/w as alcohol
   which step involves spraying alcohol onto the material to start granulating and adjusting the mixer speed and chopper speed in such a way as to promote granulation on the one hand and to inhibit blocking of the apparatus tools on the other hand. When the formation of the pellets appears slow, further isopropanol within the above mentioned amount range may be applied in portions interspersed with mixing periods until the desired pellet size distribution is achieved.
   viii) The still moist pellet material is dried in a drier with a diverted recirculating air stream with the inlet temperature not exceeding 70° C. (158° F.), the outlet end point temperature being at least 45° C. (113° F.).
   ix) Finally the dried pellet material is sieved to obtain a specification range of 500–1700 μm, preferably 600–1500 μm;

3) coating the dried and sieved pellets to achieve their prolonged action:
   x) the sieved dried pellets are coated with a mixture of acrylates using a spraying technique. Suitable acrylates include poly(ethylacrylate, methacrylate trimethylammonioethylmethacrylate chloride having a mean molecular weight within the range of 120 000 to 180 000, preferably 145 00 to 155 000, which is dissolved in a mixture of solvents, preferably organic solvents such as ethanol, isopropanol and/or acetone together with small amounts of a plastisizer such as triacetin, triethyl citrate or dibutyl phthalate or other substances which are common for this purpose, and talcum such as microtalc, whereby the appropriate amounts of unlaquered pellets:acrylic acid copolymers:emollient-:microtalc:solvent are in w/w 100 parts:3–4 parts:0.25–3.5 parts:2.7–3.3 parts:22–28parts the solvent ratio isopropanol:acetone being within the range of 1.2–1.7:0.8–1.2 v/v which solvent mixture is sprayed onto the agitated pellets (optionally in the fluid bed) in such an amount that the portion of the coating layer calculated on the basis of the total pellet weight is within the range of 2.5. to 5.0% w/w whereafter as last step.

4) the preparation of the final medicament follows:

xi) the coated pellets are charged into hard gelatin capsule. The bottom part of the capsulee is filled and subsequently the capsule is closed by means of the gelatin top part, then the capsules are sealed in blister packages.

The amount of pellets to be encapsulated is calculated in such a way that each capsule contains 20, 25, 30, 50, 75, 100 or 150 mg, preferably 50 or 100 mg triterpene glycosides as agent which is calculated as escin, i.e. just 200 mg pellet material has to be filled into relatively small capsules if the triterpene glycoside content is only 15%, see above step v)-b). To achieve a dosage amount of 30 mg agent or, for instance, approximately 417 mg coated pellets to encapsulate are sufficient to give a sustained release dosage unit of 75 mg triterperpene glycoside which is considerably increased (calculated on the basis of escin if the triterpene content of the coated pellet is in the upper limit of 18%).

The standardization amounts of dextrin may be variable and incorporated in step iii) or/and step v). Alternatively, the amount of dextrin necessary for standardization purposes can be determined and added in step iii) or in step v) and is best to be varied in only one of both steps. Best product results are obtained if the amount of dextrin is a fixed, predetermined quantity in step iii) in preparing the spraying mixture, whereas at the same time a determined amount of dextrin calculated for standardizing is added only in step v) before manufacturing the pellets. This surprising finding is demonstrated in more detail in the comparative examples below.

The following example illustrates the best mode to carry out the invention. Modifications of the invention as claimed can be made within the skills of the experts without departing from the spirit of the invention.

EXAMPLE

Preparation of Horse Chestnut Diffusion Pellets and Manufacture of the Finished Pharmaceutical Composition Firstly the extract, i.e. the concentrated tincture of *Aesculus hippocastanum* was prepared in accordance with the preceding description as outlined under paragraph 1), i) and ii) in the detailed description of the present invention in using 10 kgs of milled horse chestnut seeds. This material was then macerated and percolated by means of ca. 40% in volume methanol or isopropanol in water as cosolvent at a temperature of ca. 33° C. (91–92° F.) the amount of the total solvent being ca. 200 liters. The processes of macerating and percolating the seeds was repeatedly continued until the plant material was more or less exhausted. The extracted chestnuts were separated from the tincture and discharged. The obtained tincture was then decanted and filtered.

The liquid horse chestnut extract (HCE) was prepared by evaporating the above tincture under reduced atmospheric pressure at a protective temperature of ca. 45° C. (110–120° F.) until a content of total dry substance residue of ca 55% was obtained; for the preparation of the spray-drying mixture dextrin was added to the liquid horse chestnut extract (HCE) in a fixed amount of 5 or 20 parts per weight per 100 parts per weight total dry substance, for instance as kilograms, more specifically, 2 kgs dextrin per 20 kgs dry substance, i.e. per ca. 36–37 liters liquid extract, in this case together with demineralized water in such an amount as to adjust the spray-drying solution to a total dry substance content of 45% w/w which in this example was an amount of ca. 8 liters water to add to the preceding liquid extract, the resulting triterpene glycoside content of being 18% w/w (after removal of the solvent) in the dry extract to be made, calculated on the basis of the typical pharmacologically active agent escin, to prepare the spray-drying solution, see above step iii). The dried extract was prepared by starting with this solution mixture according to the preceding process conditions described under step iv). A free-flowing powder of homogeneous consistency was obtained the triterpene glycoside content being 19.9% w/w.

By means of this free-flowing dry horse chestnut extract (HCE) pellets were prepared in following the above process features described along the lines of steps v) to ix) under paragraph 2):

An amount of 9 kgs of the thus obtained spray-dried extract was blended together with a standardizing quantity of dextrin which in this case was ca. 180 grams to achieve a final triterpene glycoside content of 17% w/w in the pellets ready for administration and the other components such as copovidone or polyvidone acetate in a suitable amount such as ca. 300 grams and talcum in a suitable amount such as 150 grams. All these components were thoroughly mixed together, then an alcohol such as ethanol or isopropanol was sprayed onto this powdery mixture. A commercial high shear mixer was used for pelletizing and operated in such a way as to cause the formation of the wanted pellets. The amount of alcohol needed for sufficient moisture levels and effective globulization was approximately 2.5 liters in total. The moist pellet material was dried, discharged and sieved to obtain the wanted pellet core distribution.

The sieved pellets were then coated by spraying a suspension of a commercial mixture of poly(ethylacrylate, methylmethacrylate, trimethylammonioethylmeth-acrylate chloride) having a mean molecular weight of ca. 150 000 dissolved in the alcoholic mixture together with an emollient such as triethyl citrate in minor amounts and microtalc to prevent from agglomeration to get a suspension having a total content of solid substances of 2–4% w/w on the basis of the unlaquered pellet cores, i.e. ca 180–450 grams solids relating to a pellet core weight of ca 10.5 kgs to achieve a sustained release rate of the coated diffusion pellets of 30% within the first hour, see above process description, paragraph 3), step x). Alternatively, by varying the amount of coating substance within the preceding parts by weight range which can be outside of those limits, if necessary, the sustained release rate may be controlled, for instance within the wanted values of 25 to 35 or 45% w/w within the first hour.

Finally, the thus coated diffusion sustained release pellets were encapsulated as described under above paragraph 4), step xi). In the present example, the triterpene glycoside content was adjusted to 17% w/w calculated on the basis of the reference agent escin. In order to obtain the required dosage unit of 50 mg escin as triterpene glycoside agent, per capsule, 294 mg coated pellets being within the sieving range of 800–1400 μm were encapsulated and sealed into blister packages. Optionally, the coated diffusion pellets can in a conventional manner be compacted to rapidly desintegrating matrix tablets setting free the sustained release pellets comprising the escin in the wished dosage unit such as for instance 75 mg each.

The pharmaceutical formulations according to the invention may additionally contain one or more further active ingredients being processed as pellets or contained in the said compacted tablet matrix in combination with pharmaceutically acceptable carriers and other inactive ingredients. These further active ingredients may be selected from the group consisting of circulatory drugs, flavonoids, analgesics, diuretics, vitamins and anti-inflammatory agents, in particular they may be selected from the group consisting of triamterene, thiazides, rutoside, aesculine, troxerutin, dihydroergotamine, heptaminol, diclofenac, inositol nicotinate or tocopherole. Those combinatory agent may also be selected from other drugs such as the blood flow enhancing agents, antirrheumatics, cardiovascular agents etc.

COMPARATIVE EXAMPLES

There were five different batches of pellets manufactured. Batch no. 1 was produced in accordance with the preceding example as diffusion pellets in the following specifically given process which features a fixed amount of dextrin which was added as 5 parts by weight to the spraying solution, i.e. the standardization to a content of 17% escin was only carried out later on in the step to prepare the pelletization blend.

Batch no. 2 was repeated with the exception that the feature of adding dextrin to the liquid extract was changed. The amount of dextrin was doubled to 10 parts by weight compared with batch no. 1 before spray-drying and reduced by 5 parts by weight in the later step of preparing the pelletization blend for standardization purposes. This means that the agent standardization on the basis of escin was carried out partially in step iii) and also partially in step v) to blend the pelletization mixture.

Furthermore, batch no. 3 was produced in the same manner as batches no. 1 and 2 with the exception that a even greater amount of dextrin was added to the spray-drying solution, namely 21 parts by weight whereas at the same time the amount of dextrin in preparing the pelletization solution was reduced accordingly. This means that the standardization took place just iin step iii) before spray-drying.

Batch no. 4 was produced in accordance with the preceding batches, however with the exception that the amount of dextrin was drastically increased beyond the quantity sufficient as standardization and powder/pellet additive. This added amount of dextrin in step iii) before spray-drying was 30 parts by weight whereas the dextrin amount in step v) was reduced to minor amounts.

Finally, batch 5 was produced in accordance with the above batches only with the exception that no dextrin at all was added in step iii), but a respectively increased amount of dextrin was used for preparing the pelletization blend.

The results of these comparative tests are listed in the following table:

TABLE

| Run no. | Amount of dextrin added before spr. | Escin release during 1st hr | Amount of coating % | Yield of uncoated pellets |
|---|---|---|---|---|
| Batch no.1 | 5 p. by w. | 31,5% | 95% | 39,4% |
| Batch no.2 | 10 p. by w. | 35,1% | 85% | 41,2% |
| Batch no.3 | 21 p. by w. | 33,7% | 110% | 26,5% |
| Batch no.4 | 30 p. by w. | 42,4% | 120% | 26,2% |
| Batch no.5 | none | — | — | — |

The surface and consistency quality of batch no. 1 was excellent; the pellets showed a surprisingly round and smooth surface; the pellet surface with batch no. 2 was quite round and the surface still homogenous;

the pellets of batch no. 3 showed a surface consistency which was only just satisfactory whereas the surface of the pellet material according to batch no. 4 was quite poor because of coarseness;

the dried extract resulting from run 5, i.e. batch no. 5 was so poor that processing to pellets could not be brought further because of machine blocking; for this reason, no pellet data were available from this run.

In all batches nos. 1 to 4 the release rates after 1 hour, measured in a commercial tester, were determined. Release rates between 30 and up to 35% are considered to be acceptable. The comparative percentages of dry coating substance, also called laquer is based on an amount of 100% which is needed to obtain a release rate of approximately 30%.

These data show that a fixed amount of 5 weight parts and also an amount of up to 10 weight parts dextrin added to the spray-drying solution render the best results. Under these conditions the standardization of the agent is shifted to step v) to prepare the pelletization blend. It is, however, to be noted that an amount of only 5 parts by weight dextrin to the spray-drying solution leads to an almost ideal coating amount of 100%, precisely 95% whereas the double amount added to the spraying solution according to batch 2 reduces the coating quantity needed, but leads to the limit to accept the release rate during the first hour. The pellets made in accordance with batch no. 3 show a release rate which is satisfying, but their yield still before coating is not acceptable in the sense of an economical manufacture. The same holds true with respect to batch no. 4 which rendered a disappointing yield, but also an unacceptable release rate and moreover too high amounts of the expensive coating material.

Further Comparative Data:

In order to compare the influence of the amount of dextrin added to the spraying solution, the tapped bulk density, expressed in grams per milliliter, was determined:

| Addition of dextrin in parts p. by w. | bulk density in grams/ml |
|---|---|
| 7 parts p. by w. | 0.48 g/ml |
| 20 parts p. by w. | 0.41 g/ml |

These comparative data show that against all expectations the tapped bulk density is increased if the amount of dextrin added to the spray-drying solution is reduced and vice versa. The expert would actually come to the conclusion that regarding the light spray-dried horse chestnut extract (HCE) the addition of higher dextrin amounts would increase the density. This result of the inventive process is completely surprising for the persons skilled in the art. It was further fully unexpected that the control and selection of inventive process features would lead to those satisfying yields in manufacturing such a highly sensitive plant extract to a safe sustained release product having ideal therapeutical properties, in particular regarding the fact that seed extracts of in particular *Aesculus hippocastanum* are difficult to be processed.

While the invention has been described in connection with the above embodiments it will be understood that it is capable of further modifications and this application is intended to cover any variations, uses, or adaptions of the inventions following, in general, the principles of the invention and including such departures from the present disclosure as come within known and customary practice within the art to which the invention pertains and as may be applied to the essential features hereinbefore set forth, and as follows in the scope of the appended claims.

What is claimed is:

1. A method of producing a pharmaceutical formulation containing escin as a pharmaceutically active ingredient, for treatment of prophylaxis of venous circulatory disorders, venous insufficient or inflammations, edema including brain edema, or swellings, in which said formulation is prepared by a process comprising:
   i) milling horse chestnut seeds to a maximum particle size of 6 mm and a minimum particle size of 0.3 mm, then macerating and percolating for 1 to 2 days the milled seeds with a mixture of alcohol and water as solvent, the alcohol content being 35–65% v/v, at a temperature of 30–40° C., to obtain a horse chestnut extract tincture, whereby 1500 parts by weight—2000 parts by weight is extracted by 4000 to 5000 parts by volume;
   ii) concentrating the thus obtained liquid horse chestnut tincture under reduced atmospheric pressure by evaporation with a temperature of 45–60° C. until a content of total dry residue of 50% to 63% w/w in the liquid extract is obtained;
   iii) adding: a) dextrin in a ratio of 1 to 25 parts by weight per 100 parts by weight to the total dry substance calculated on the basis of the liquid extract obtained according to ii) above, optionally together with b) demineralized water in such an amount as to adjust the spray-drying solution to a total dry substance content of 38–48% w/w and a triterpene glycoside content of 15–20% w/w % in the dry extract to be made, calculated on the basis of the pharmacologically active agent escin, to prepare the liquid extract mixture for spray-drying;
   iv) spray-drying the preceding liquid mixture at a temperature of 40–60° C., the inlet air having an $O_2$ content of <10% and a temperature of 180–210° C., the outlet air having a temperature of 75–95° C.;
   v) adding
      a) dextrin to
      b) the free-flowing spray-dried extract obtained through iv) so that the complete mixture to be pelletized has a total standardized content of 15–19% w/w triterpene glycosides, calculated on the basis of the agent escin to form a standardized mixture;
   vi) blending the above standardized mixture of a) dextrin and b) spray-dried extract together with
      c) polyvinylpyrrolidone, selected from the group consisting of povidone and a copolymerisate of vinyl pyrrolidone and vinyl acetate and
      d) talcum so that the weight ratio is in w/w 0.5–10 parts a): 50–150 parts b): 1–15 parts c): 0.5–10 parts d);
   vii) pelletizing the mixture of a): b): c): d) by adding an alcohol for moistening the blend in a mixer/granulator apparatus or marumerizer, spheronizer or other pelletizing machine to form a moist pelletized material;
   viii) drying the moist pelletized material in a drier using a diverted recirculating air stream from the drier wherein the inlet temperature does not succeed 70° C., the outlet end point temperature being at least 45° C. to form a dried pellet material;
   ix) sieving the dried pellet material to obtain a specification range of 500–1700 μm to obtain sieved pellets;
   x) coating the sieved pellets by spraying technique using a mixture of acrylates, dissolved in a mixture of organic solvents together with small amounts of a plasticizer so that the portion of the coating calculated on the basis of the total pellet weight is within the range of 2.5 to 5.0% w/w to form coated pellets and finally filling the coated pellets into hard gelatin capsule bottom parts, closing the capsules by means of the gelatin top parts or compacting the coated pellets together with usual pharmaceutically acceptable disintegrating matrix components to sustained release tablets.

2. A method according to claim 1, wherein said pharmaceutically acceptable acrylate polymer is selected from the group consisting of polymers of ethylacrylate, of ethylmethacrylate, of trimethylammonium ethyl methacrylate and of trimethylammonium ethyl acrylate.

3. A method according to claim 1, wherein; in iii), the dextrin is added to the spray-drying solution in a fixed amount related to each production batch, in v) the dextrin is added in such amounts as to standardize the triterpene glycoside content in the coated diffusion pellets to 17%, and in vi said copolymerisate 60/40, within a mean molecular weight of 45,000 and 75,000 is added, the pelletization being carried out using a high shear mixer, the sieve range of the encapsulated pellets being between 800–1400 μm and the dosage unit of each sustained release hard gelatin capsule or matrix tablet being 30, 50, 75 or 100 mg escin.

4. Pharmaceutical formulation containing standardized dry horse chestnut extract for the treatment of venous circulatory disorders, venous insufficiency, inflammations, edema including brain edema or swellings, characterized in that it is manufactured according to the process as claimed in claim 1.

5. Pharmaceutical formulation according to claim 4, characterized in that it additionally contains at least one additional active ingredient being processed as pellets or contained in the said compacted tablet matrix in combination with pharmaceutically acceptable carrier and other inactive ingredients.

6. Pharmaceutical formulation according to claim 5, characterized in that the at least one additional active ingredient is selected from the group consisting of circulatory drugs, flavonoids, analgesics, diuretics, vitamins and anti-inflammatory agents.

7. Pharmaceutical formulation according to claim 6, characterized in that the at least one additional active ingredient is selected from the group consisting of triamterene, thiazides, rutoside, aesculine, troxerutin, dihydroergotamine, heptaminol, diclofenac, insitol nicotinate and tocopherole.

8. A method for the therapeutical and prophylactic treatment of venous circulatory disorders, venous insufficiency, inflammations, swellings or edema, including brain edema, wherein a pharmaceutical formulation as claimed in claim 4 is administered as diffusion pellets in unit doses of 20–150 mg escin as reference substance to patients.

9. A method according to claim 1, wherein the polyvinylpyrrolidone is a polyvidone acetate having a mean molecular weight of 40,000 to 80,000 as calculated by a light dispersion method.

10. A method according to claim 1, wherein the mixture of acrylates is selected from the group consisting of polyethylacrylate and methacrylate trimethyl-ammoinoethylmethacrylate chloride having a mean molecular weight within the range of 120,000 to 180,000 as calculated by a light dispersion method.

11. A method according to claim 1, wherein the plasticizer is selected from the group consisting of triacetin, triethyl-citrate and dibutyl phthalate.

* * * * *